US008616051B2

(12) United States Patent
Kimour et al.

(10) Patent No.: US 8,616,051 B2
(45) Date of Patent: Dec. 31, 2013

(54) METHOD OF ANALYZING A NUMBER OF HYDROCARBONS CONTAINED IN A DRILLING FLUID, AND ASSOCIATED DEVICE

(75) Inventors: Farouk Kimour, Paris (FR); Jerome Breviere, Taverny (FR)

(73) Assignee: Geoservices Equipments, Roissy en France (FR)

( * ) Notice: Subject to any disclaimer, the term of this patent is extended or adjusted under 35 U.S.C. 154(b) by 642 days.

(21) Appl. No.: 12/838,063

(22) Filed: Jul. 16, 2010

(65) Prior Publication Data

US 2011/0000294 A1    Jan. 6, 2011

Related U.S. Application Data

(63) Continuation-in-part of application No. PCT/FR2008/050079, filed on Jan. 18, 2008.

(51) Int. Cl.
*E21B 47/00* (2012.01)
*G01N 30/02* (2006.01)

(52) U.S. Cl.
USPC ........................................ 73/152.04; 73/23.35

(58) Field of Classification Search
USPC ................... 73/152.04, 23.35, 23.39, 23.41
See application file for complete search history.

(56) References Cited

U.S. PATENT DOCUMENTS

| | | | |
|---|---|---|---|
| 4,384,471 A | | 5/1983 | Wentzel |
| 4,635,735 A | * | 1/1987 | Crownover ...................... 175/48 |
| 4,765,182 A | * | 8/1988 | Boone ........................ 73/152.04 |
| 4,837,157 A | * | 6/1989 | Turnell et al. ................... 436/20 |
| 4,887,464 A | | 12/1989 | Tannenbaum et al. |
| 5,190,882 A | * | 3/1993 | Schulz et al. ................. 436/139 |
| 5,399,256 A | * | 3/1995 | Bohs et al. ..................... 204/409 |
| 5,405,782 A | * | 4/1995 | Kohn et al. .................... 436/161 |
| 5,547,877 A | * | 8/1996 | Friedman et al. ............. 436/126 |

(Continued)

FOREIGN PATENT DOCUMENTS

| | | |
|---|---|---|
| EP | 1 645 718 A2 | 4/2006 |
| FR | 2 799 790 A1 | 4/2001 |

(Continued)

OTHER PUBLICATIONS

Office Action issued on Jan. 11, 2012 for Japanese patent application No. 2010-542658 which is correspondent of U.S. Appl. No. 12/838,063.

(Continued)

*Primary Examiner* — John Fitzgerald
(74) *Attorney, Agent, or Firm* — Sughrue Mion, PLLC

(57) ABSTRACT

The method includes extraction of gases contained in a mud, in order to obtain a gas stream of extracted gases containing hydrocarbons to be analyzed and at least one parasitic compound. The method includes transporting the gas stream through a transport line (54) and passing it through a separation column (121) in order to separate the hydrocarbons to be analyzed according to their elution times in the separation column (121). The parasitic compound is likely to have an elution time in the separation column (121) between the elution time for the first hydrocarbon to be analyzed and the elution time of the final hydrocarbon to be analyzed. The method includes passing the gas stream over a surface (141) for chemical and/or physical interaction with the parasitic compound in order to selectively retain the or each parasitic compound without retaining the hydrocarbons to be analyzed.

13 Claims, 4 Drawing Sheets

(56) References Cited

U.S. PATENT DOCUMENTS

| | | | |
|---|---|---|---|
| 5,595,709 | A | 1/1997 | Klemp |
| 5,719,322 | A * | 2/1998 | Lansbarkis et al. .......... 73/23.39 |
| 6,443,001 | B1 | 9/2002 | Duriez et al. |
| 7,392,138 | B2 * | 6/2008 | Frechin et al. .................... 702/9 |
| 7,779,667 | B2 * | 8/2010 | Evrard ......................... 73/19.09 |
| 7,905,133 | B2 * | 3/2011 | Chordia et al. ............. 73/61.56 |
| 2003/0230524 | A1 * | 12/2003 | Soga et al. ................. 210/198.2 |
| 2005/0106741 | A1 * | 5/2005 | Dijke ............................. 436/140 |
| 2006/0075801 | A1 | 4/2006 | Evrard et al. |
| 2007/0183928 | A1 * | 8/2007 | Neyer et al. ..................... 422/70 |
| 2011/0094736 | A1 * | 4/2011 | Evrard ......................... 166/267 |

FOREIGN PATENT DOCUMENTS

| | | |
|---|---|---|
| GB | 1 380 581 A | 1/1975 |
| WO | 95/30147 | 11/1995 |
| WO | 2006114512 A1 | 11/2006 |

OTHER PUBLICATIONS

A. Voelkel et al.; "Inverse gas chromatography for the examination of fractions separated from oil vacuum distillation residues"; Journal of Chromatography; vol. 768 (1997); pp. 271-281.

Wenger, Lloyd et al., "Impact of Modern Deepwater Drilling and Testing Fluids on Geochemical Evaluations," Organic Geochemistry, vol. 35, 2004, pp. 1527-1536.

Lloyd M. Wenger, Cara L. Davis, Joseph M. Evensen, James R. Gormly, Paul J. Mankiewicz, "Impact of Modern Deepwater Drilling and Testing Fluids on the Geochemical Evaluations," Organic Geochemistry, vol. 35 (2004), pp. 1527-1536.

* cited by examiner

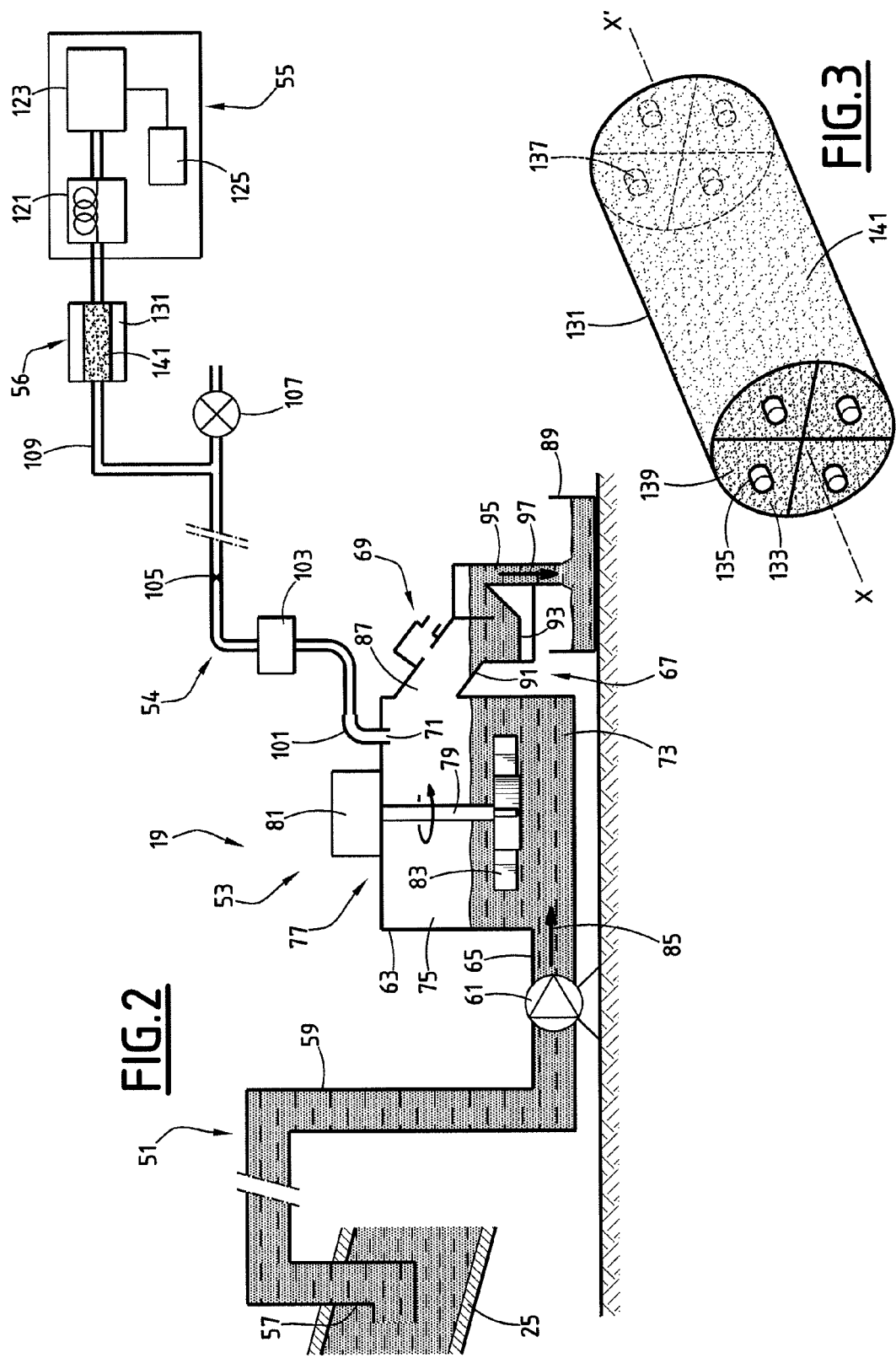

US 8,616,051 B2

METHOD OF ANALYZING A NUMBER OF HYDROCARBONS CONTAINED IN A DRILLING FLUID, AND ASSOCIATED DEVICE

CROSS REFERENCE TO RELATED APPLICATIONS

This application is a Continuation-in-Part of International Application No. PCT/FR2008/050079 filed Jan. 18, 2008, the content of which is incorporated herein by reference in its entirety.

BACKGROUND OF THE INVENTION

The present invention relates to a method for analysing a plurality of hydrocarbons contained in a drilling fluid, of the type comprising the following steps:
- extraction of the gases contained in the fluid in an extractor in order to obtain continuously, at an outlet of the extractor, a gas stream of extracted gases containing hydrocarbons to be analysed and at least one interfering compound other than water and more polar than the hydrocarbons to be analysed;
- transport of the gas stream through a transport line connected to the outlet of the extractor;
- passing of the gas stream into a separation column connected to the transport line, in order to separate the hydrocarbons to be analysed according to their elution time in the separation column;
- successive detection and/or quantification of each hydrocarbon to be analysed in a detector placed at the outlet of the separation column;

the or each interfering compound being liable to have an elution time in the separation column of between the elution time in the separation column of the first hydrocarbon to be analysed and the elution time in the separation column of the last hydrocarbon to be analysed.

When drilling an oil well or a well for another effluent (in particular gas, vapour, water), it is known to carry out an analysis of the gaseous compounds contained in the drilling muds emerging from the well. This analysis makes it possible to reconstruct the geological sequence of the formations which are passed through during the drilling operation, and plays a part in determining the possibilities for exploiting the deposits of fluids encountered.

This analysis, which is carried out continuously, comprises two main phases. The first phase consists of extracting the gases carried by the mud (for example hydrocarbons, carbon dioxide, hydrogen sulphide, helium and nitrogen). The second phase consists of qualifying and quantifying the gases extracted. In the first phase, mechanically agitated degassers of the aforementioned type (FR-A-2 799 790) are frequently used. The gases extracted from the mud, which are mixed with a carrier gas introduced into the enclosure, are conveyed by suction via the gas extraction pipe to an analyser which permits the extracted gases to be quantified.

BRIEF SUMMARY OF THE INVENTION

To this end, the invention relates to a method of the aforementioned type, characterised in that the method comprises the step of passing the gas stream over a surface of chemical and/or physical interaction with the interfering compound, the interaction surface being placed in contact with the gases between the outlet of the extractor and an inlet of the separation column, to retain selectively the or each interfering compound without retaining the hydrocarbons to be analysed, in order to prevent the elution of the or each interfering compound in the separation column between the elution time of the first hydrocarbon to be analysed and the elution time of the last hydrocarbon to be analysed.

When drilling an oil well, it is known for example to analyse and quantify the $C_1$ to $C_5$ hydrocarbons in succession. In some cases, the analysis unit further makes it possible to determine the presence of any $C_6$ to $C_8$ hydrocarbons.

Such analyses are sometimes not entirely satisfactory, in particular when drilling muds produced on the basis of synthetic oils are used.

Such muds are liable to contain interfering compounds having an elution time of between the elution time of the first hydrocarbon to be analysed and the elution time of the last hydrocarbon to be analysed. These interfering compounds are present by nature in the constituents of the drilling mud, or result from chemical reactions between the compounds of the drilling mud when this mud is exposed to the high temperatures and pressures encountered at the bottom of the well.

In order to overcome this problem, an analysis method in which successive samples of drilling mud taken at the outlet of a well are treated with the aid of an organic solvent in order to extract the interfering compounds which disrupt the analysis of the hydrocarbons is known from the article "Impact of Modern Deepwater Drilling and Testing Fluids on the Geochemical Evaluations", published in Organic Geochemistry, Volume 35 (2004), pages 1527-1536. Such a technique is tedious to put into practice, and cannot be carried out on-line.

An alternative proposed in this article consists of mathematically processing the elution spectra obtained at the detector at the outlet of the separation column in order to subtract the peaks produced by the interfering compounds from these spectra. Such a technique, however, is still not very accurate, and is still subject to the precise identification and quantification of these interfering compounds.

It is therefore an object of the invention to obtain a method for analysing a plurality of hydrocarbons contained in a drilling fluid which makes it possible in a simple manner to obtain a precise qualification and/or quantification of the hydrocarbons to be analysed, the analysis being sufficiently fast to be carried out on-line.

To this end, the invention relates to a method of the aforementioned type, characterised in that the method comprises the step of passing the gas stream over a surface of chemical and/or physical interaction with the interfering compound, the interaction surface being placed in contact with the gases between the outlet of the extractor and an inlet of the separation column, to retain selectively the or each interfering compound without retaining the hydrocarbons to be analysed, in order to prevent the elution of the or each interfering compound in the separation column between the elution time of the first hydrocarbon to be analysed and the elution time of the last hydrocarbon to be analysed.

The method according to the invention may comprise one or more of the following characteristics, taken in isolation or in any technically possible combination(s):
- the interaction surface is suitable for interacting with the or each interfering compound via a hydrogen-bond, dipolar-attraction or ion-exchange mechanism, in order to retain selectively the or each interfering compound without retaining each hydrocarbon to be analysed;
- when the gas stream passes over the interaction surface, more than 90 mole % of each polar interfering compound is retained on the interaction surface, less than 10 mole % of the hydrocarbons to be analysed being retained on the interaction surface;

the interaction surface comprises unmodified silica, silica modified with electron donor groups, silica doped with magnesium, alumina, or a styrene/divinylbenzene polymer;

the interaction surface is placed in a removable cartridge mounted on the transport line between the outlet of the extractor and the separation column;

the interaction surface is arranged in a pre-separation column mounted upstream from the separation column;

the interaction surface comprises polyethylene glycol;

the pre-separation column has a Chrompack index of greater than 8, advantageously greater than 20;

the hydrocarbons to be analysed comprise $C_1$ to $C_n$ hydrocarbons, n being less than or equal to 10, advantageously n being less than or equal to 8; and the or each polar interfering compound comprises at least an oxygen atom, a nitrogen atom or a sulphur atom.

The invention further relates to a unit for the analysis of a plurality of hydrocarbons contained in a drilling fluid, of the type comprising:

an extractor for the gases contained in the fluid, the extractor having a gas extraction outlet in order to obtain, continuously at the outlet, a gas stream of extracted gases containing hydrocarbons to be analysed and at least one interfering compound other than water and more polar than the hydrocarbons to be analysed;

a transport line for the gas stream, connected to the outlet of the extractor;

an analyser comprising:
 a separation column connected to the transport line for separating the hydrocarbons to be analysed according to their elution time in the separation column;
 a detector placed at the outlet of the separation column for detecting and/or quantifying in succession each hydrocarbon to be analysed;

the interfering compound being liable to have an elution time in the separation column of between the elution time in the separation column of the first hydrocarbon to be analysed and the elution time in the separation column of the last hydrocarbon to be analysed, characterised in that the analysis unit comprises a surface of chemical and/or physical interaction with the interfering compound, the interaction surface being placed in contact with the gases between the outlet of the extractor and an inlet of the separation column, in order to retain selectively the or each interfering compound without retaining the hydrocarbons to be analysed, in order to prevent the elution of the or of each interfering compound in the separation column between the elution time of the first hydrocarbon to be analysed and the elution time of the last hydrocarbon to be analysed.

The unit according to the invention may comprise one or more of the following characteristics, taken in isolation or in any technically possible combination(s):

it comprises a removable cartridge containing the interaction surface, the removable cartridge being mounted in series on the transport line upstream from the separation column; and it comprises a pre-separation column containing the interaction surface, the pre-separation column being mounted in series on the transport line or downstream from the transport line, upstream from the separation column.

BRIEF DESCRIPTION OF THE DRAWINGS

The invention will be better understood on reading the following description, which is given solely by way of example, and is written with reference to the appended drawings, in which:

FIG. 2 is a schematic view in vertical section of the main elements of the analysis unit according to the invention;

FIG. 3 is a perspective three-quarter-face view of a removable purification cartridge arranged in the analysis unit of FIG. 2;

DETAILED DESCRIPTION OF THE INVENTION

In everything which follows, the terms "upstream" and "downstream" are understood with respect to the normal direction of circulation of a fluid in a pipe.

An analysis unit according to the invention is used for example in a drilling installation 11 for an oil production well.

Figure 1:
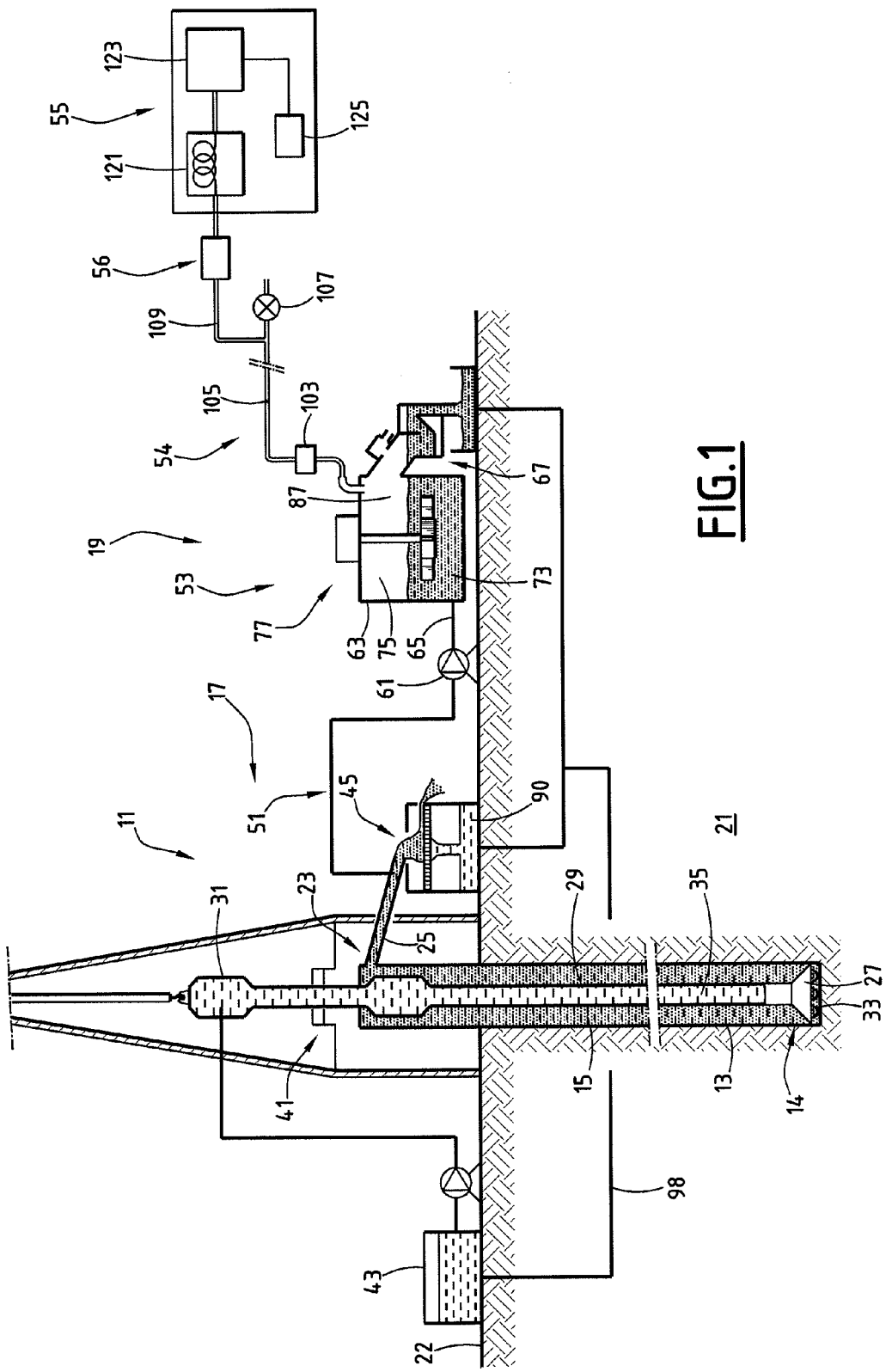
FIG. 1 is a schematic view in vertical section of a drilling installation, provided with a first analysis unit according to the invention.

As illustrated in FIG. 1, this installation 11 comprises a drilling pipe 13 arranged in a cavity 14 bored by a rotary drilling tool 15, a surface installation 17 and a first analysis unit 19 according to the invention.

The drilling pipe 13 is arranged in the cavity 14 formed in the substratum 21 by the rotary drilling tool 15. This pipe 13 comprises, at the surface 22, a well head 23 provided with a discharge pipe 25.

The drilling tool 15 comprises a drilling head 27, a drill string 29 and a liquid injection head 31.

The drilling head 27 comprises means 33 for drilling through the rocks of the substratum 21. It is mounted on the lower portion of the drill string 29 and is positioned in the bottom of the drilling pipe 13.

The string 29 comprises a set of hollow drilling tubes. These tubes delimit an internal space 35 which makes it possible to bring a liquid from the surface 22 to the drilling head 27. To this end, the liquid injection head 31 is screwed onto the upper portion of the string 29.

The surface installation 17 comprises means 41 for supporting the drilling tool 15 and driving it in rotation, means 43 for injecting the drilling liquid and a shale shaker 45.

The injection means 43 are hydraulically connected to the injection head 31 in order to introduce and circulate a liquid in the inner space 35 of the drill string 29.

The shale shaker 45 collects the liquid laden with drilling residues which emerges from the discharge pipe 25, and separates the liquid from the solid drilling residues.

As illustrated in FIG. 2, the analysis unit 19 comprises means 51 for sampling the mud which are tapped into the discharge pipe 25, a gas extractor 53 and a line 54 for transporting the extracted gases which is connected to the extractor. The analysis unit 19 further comprises an analyser 55 for the extracted gases, into which the transport line 54 opens, and, in accordance with the invention, means 56 for purifying the extracted gases, which are mounted in series on the line 54 between the extractor 53 and the analyser 55.

The sampling means 51 comprise a liquid sampling head 57, arranged protruding into the discharge pipe 25, a connecting tube 59 and a peristaltic pump 61, the flow rate of which is adjustable.

In a variant, the sampling means 51 are tapped into a receiving tank for the liquid, into which the discharge pipe 25 opens. In another variant, the sampling means 51 are tapped into a tank of the mud injection means 43.

The extractor 53 comprises an enclosure 63, a pipe 65 for supplying mud into the enclosure 63, a pipe 67 for evacuating the mud from the enclosure 63, an inlet 69 for introducing a carrier gas into the enclosure 63 and an outlet 71 for extracting the extracted gases from the enclosure 63.

The enclosure 63 comprises a hermetic receptacle, the internal volume of which is for example between 0.4 litres and 3 litres. This enclosure 63 comprises a lower portion 73, in which the mud circulates, and an upper portion 75, which has an ullage space. The enclosure 63 is further provided with agitating means 77, comprising an agitator 79, mounted so as to protrude into the enclosure 63 and driven in rotation by a motor 81 mounted on the upper portion 75 of the enclosure 63. The agitator 79 comprises an agitating mechanism 83 immersed in the mud.

The mud supply pipe 65 extends between the outlet of the peristaltic pump 61 and an entry opening 85, formed in the lower portion 73 or upper portion 75 of the enclosure 63.

This supply pipe 65 may be provided with means for heating the mud (not shown) in order to bring the temperature of this mud to values of between 25 and 150° C., preferably of between 60 and 90° C.

The evacuation pipe 67 extends between an overflow passage 87, formed in the upper portion 75 of the enclosure 63, and a retention basin 89 for receiving the mud evacuated from the device 53.

In a variant, the retention basin 89 is formed by a receiving tank 90 for the liquids extracted from the shale shaker 45, shown in FIG. 1.

In this example, the evacuation pipe 67 comprises in succession an upstream portion 91 inclined downwards, which is at an angle of approximately 45° to the horizontal, an angled portion 93 forming a siphon, and a substantially vertical downstream portion 95, open at its lower end 97 arranged facing the basin 89, above the level of the liquid contained in the basin 89.

The mud collected in the retention basin 89 and in the tank 90 is recycled to the injection means 43 by a mud recirculation pipe 98.

The introduction inlet 69 opens into the upper portion 75 of the enclosure 63. It is advantageously connected to a source (not shown) of a carrier gas such as nitrogen or helium. In a variant, the inlet 69 opens into the atmosphere located around the enclosure 63.

The outlet for evacuating the extracted gases 71 is delimited in an upper portion of the enclosure, in the vicinity of the agitator 75. It comprises a fitting 101 for connection to the transport line 54.

The line 54 is mounted on the fitting 101. The line 54 is capable of continuously sampling a stream of gases extracted from the mud in the upper portion 75 of the enclosure in order to convey this stream to the analyser 55.

As will be seen below, this gas stream contains hydrocarbons to be analysed, water vapour, and, upstream from the purification means 56, at least one interfering compound other than water and more polar than the hydrocarbons to be analysed, which is liable to disrupt the analysis of the hydrocarbons to be analysed. The polar interfering compounds referred to here will be defined more precisely below.

The hydrocarbons to be analysed are for example $C_1$ to $C_n$ hydrocarbons, with n being less than or equal to 10, advantageously with n being less than or equal to 8.

As will be seen further below, the polar interfering compounds other than water will depend on the nature of the drilling mud used and the conditions to which the mud is subjected. These compounds comprise at least one heteroatom, in particular an oxygen, nitrogen or sulphur atom.

In particular, these interfering compounds further comprise a $C_1$ to $C_{10}$, in particular $C_1$ to $C_5$, hydrocarbon group which is linear, branched or cyclic, saturated or unsaturated. They comprise for example a $C_1$ to $C_{10}$ alkyl or alkene or alkyne group substituted by one or more —OH, —$NH_2$, —NH—$R_1$, —$NR_2R_3$, —$OR_4$, —SH, —$SR_5$, —$R_6COO(R_7)$ group(s) in which $R_1$ to $R_7$, independently of one another, represent $C_1$ to $C_{10}$ alkyl groups.

The interfering compounds are in particular alcohols, ethers or esters which comprise a number of carbon atoms of less than 10, in particular a number of carbon atoms of less than 5.

In this example, the transport line 54 connects the enclosure 63 arranged in the vicinity of the well head 23, in the explosive zone, to the analyser 55, which is arranged spaced apart from the well head 23, in a non-explosive zone, for example in a pressurised cabin. In a variant, the line 54 is very short and the analyser 55 is placed in the explosive zone in the vicinity of the well head.

The transport line 54 is preferably produced on the basis of a material which is inert towards the gaseous compounds extracted from the mud, such as steel, polyethylene (PE) or PTFE. It has for example a length which varies between 10 cm and 500 m.

The transport line 54 is provided, from upstream to downstream, with a water trap 103, a flow rate controller 105 located in the vicinity of the enclosure 63, a vacuum pump 107 for conveying the extracted gases, and a branch connection 109 for connection to the analyser 105 opening upstream from the pump 107.

The water trap 103 comprises at least one cold water condensation surface in order to eliminate the water vapour present in the extracted gases substantially by condensation.

The flow rate controller 105 is formed by a tube having a constriction of calibrated cross-section. The controller sets a volume flow rate for the flow of extracted gases which circulates in the line 54. This flow rate is for example of between 300 $cm^3$ per minute and 2000 $cm^3$ per minute, and advantageously equal to 500 $cm^3$ per minute.

The pump 107 permits conveying by suction of the gases extracted from the enclosure 63 to the analyser 55. It is placed in the vicinity of the analyser 55. It has an inlet connected to the line 54 in parallel to the branch connection 109 and an evacuation outlet which opens into the atmosphere.

The branch connection 109 opens upstream from the inlet into the pump 107. It is capable of sampling approximately 10% of the volume flow rate of extracted gases circulating in the line 54, the rest of the flow of extracted gases circulating through the pump 107 to be evacuated into the atmosphere.

The analyser 55 comprises a separation column 121 for the hydrocarbons to be analysed, a detector 123 for successive detection of the hydrocarbons which are separated in the separation column 121, and means 125 for qualification and/or quantification of the hydrocarbons to be analysed which are detected by the detector 123.

The separation column 121 is a gas-chromatography separation column. This column is for example charged with the aid of a stationary phase in the form of a gel which permits the selective dissolution of the hydrocarbons in the gel in order to retain them selectively (gas-liquid chromatography). In a variant, the column has a solid coating capable of interacting with the hydrocarbons to be analysed in order to retain them selectively according to their affinity with the coating (gas-solid chromatography).

The separation column is capable of eluting in succession the hydrocarbons to be analysed according to the number of atoms which they comprise (from $C_1$ to $C_n$), starting from a stream injected at the inlet containing all the hydrocarbons to be analysed at a given moment. The hydrocarbons to be analysed emerge from the column 121 at distinct elution times of between 10 s and 100 s.

In the context of the present invention, and in everything which follows, "polar interfering compounds" are understood to mean compounds which are more polar than the hydrocarbons to be analysed and liable to have an elution time in the separation column 121 of between the elution time of the first hydrocarbon to be analysed, namely the $C_1$ hydrocarbon, and the elution time of the last hydrocarbon to be analysed, namely the $C_n$ hydrocarbon, if these polar interfering compounds were to be injected into the column 121 at the same time as the hydrocarbons to be analysed.

The detector 123 is for example a flame ionisation detector (FID), or alternatively a thermal conductivity detector (TCD). The detector may possibly be a mass spectrograph, depending on the analysis required on the gases.

The qualification and/or quantification means 125 are capable of qualifying the $C_1$ to $C_n$ hydrocarbons with n being less than or equal to 10, advantageously with n being less than or equal to 8, in order to detect their presence in the gas stream, and of quantifying the relative contents of at least the $C_1$ to $C_5$ hydrocarbons.

The purification means 56 are capable of selectively retaining the polar interfering compounds present in the gas stream which are liable to have an elution time in the separation column 121 of between the elution time of the first hydrocarbon to be analysed and the elution time of the last hydrocarbon to be analysed.

In the example illustrated by FIG. 2, the purification means 56 comprise a cartridge 131 mounted in series on the branch connection 109, downstream from the connection to the vacuum pump 107, and upstream from the connection to the separation column 121.

As illustrated by FIG. 3, the cartridge 131 comprises four axial compartments 133 distributed about an axis X-X', each being capable of being mounted removably in series on the branch connection 109.

To this end, each compartment 133 comprises an upstream fitting 135 and a downstream fitting 137 for connection respectively to two successive sections of the branch connection 109. These fittings 135, 137 are for example of Luer type or Legris quick-acting couplings.

Each compartment 133 defines an internal volume 139 containing a solid in the form of powder or granules. The solid delimits a surface 141 of chemical and/or physical interaction with the polar interfering compound, which is to be placed in contact with the gas stream in order to be swept by this stream.

According to the invention, the interaction surface 141 is capable of selectively retaining the polar interfering compounds without retaining the hydrocarbons to be analysed.

Thus, when a gas stream containing hydrocarbons to be analysed and polar interfering compounds is introduced into a compartment 133 through the downstream fitting 135, then circulates in this compartment 133 at a flow rate of between 20 cm³ per minute and 1000 cm³ per minute, in particular 50 cm³ per minute, more than 90 mole % of the hydrocarbons to be analysed exit through the outlet fitting 137, whereas less than 10% of the polar interfering compounds exit through the fitting 137 after a time equal to twice the dwell time in the internal volume.

The interaction surface 141 has a polarity suitable for selectively retaining the polar interfering compounds.

It is for example produced on the basis of silica, on the basis of alumina or on the basis of a styrene/divinylbenzene polymer (SDVB). In the case of silica, the surface 141 is advantageously produced on the basis of native or non-substituted silica in order to have covalent Si—OH bonds. In a variant, the surface 141 is produced based on silica doped with magnesium of type $SiC_3Mg$ (sold under the name FLORISIL®).

In another variant, the surface 141 is produced on the basis of silica modified by electron donor groups such as groups bearing at least one —C≡N, —OH, —NH$_2$, -cyclohexyl, —NHR$_1$, —NR$_2$R$_3$, —NH—R$_4$—NH$_2$, —NH—C$_6$H$_4$B(OH)$_2$, —COOH, —SO$_3^-$R$_5^+$ or —C$_6$H$_4$—SO$_3^-$R$_6^+$ function, where R$_1$ to R$_4$, independently of one another, are C$_1$ to C$_4$ alkyls, and R$_5^+$ and R$_6^+$ are cations of the type H$^+$ or Na$^+$. Thus, the surface 141 advantageously has groups of the type —Si—(C$_1$ to C$_4$ alkyl)-R, in which R is for example a —C≡N (advantageously not protected), —OH, —NH$_2$, —O—CH$_2$—CH(OH)—CH$_2$(OH), —NHR$_1$, —NR$_2$R$_3$, in particular —N(CH$_2$CH$_3$)$_2$, —NH—R$_4$—NH$_2$, in particular —NH—(CH$_2$)$_2$—NH$_2$, —NH—C$_6$H$_4$B(OH)$_2$, —COOH, —SO$_3^-$R$_5^+$, in particular —SO$_3^-$Na$^+$, —C$_6$H$_4$—SO$_3^-$R$_6^+$, in particular —C$_6$H$_4$—SO$_3^-$R$_6^+$ function, where R$_1$ to R$_4$, independently of one another, are C$_1$ to C$_4$ alkyls, and R$_5^+$ and R$_6^+$ are cations of the type H$^+$ or Na$^+$. The surface 141 may also advantageously have groups of —Si-cyclohexyl type.

The surface 141 is thus capable of interacting by dipolar-attraction or hydrogen-bond mechanisms with the oxygen, nitrogen or sulphur atoms present in the polar interfering compounds.

In a variant, Van der Waals forces or electrostatic forces of ionic interaction are used in order to interact with the polar interfering compounds.

It should be noted that this interaction takes place by the simple circulation of the gas stream along the solid surface 141, without the use of liquid or gaseous solvent.

A first compartment 133 is mounted in series on the branch connection 109 by means of the fittings 135, 137. The interaction surface 141 is then capable of retaining the polar interfering compounds present in the stream until it becomes saturated. In this case, a second compartment 133 is connected to the branch connection 109. The cartridges 131 are removable, and may be replaced by simply demounting them once all the compartments 133 of one and the same cartridge 131 have been used.

In a variant, the cartridge 131 comprises a single compartment 133.

The analysis method according to the invention, carried out during the operation of drilling a well, will now be described as an example, with reference to FIG. 1.

In order to carry out the drilling operation, the drilling tool 15 is driven in rotation by the surface installation 41. A drilling liquid is introduced into the inner space 35 of the drill string 29 by the injection means 43. This liquid moves downwards as far as the drilling head 27, and passes into the drilling pipe 13 through the drilling head 27. This liquid cools and lubricates the drilling means 33. Then the liquid collects the solid cuttings resulting from the drilling operation and moves back upwards through the annular space defined between the drill string 29 and the walls of the drilling pipe 13, then is evacuated through the discharge pipe 25. The liquid containing the cuttings then forms the drilling mud to be analysed.

With reference to FIG. 2, the peristaltic pump 61 is then activated in order to sample continuously a given fraction of the drilling mud circulating in the pipe 25.

This mud fraction is conveyed to the enclosure 63 via the supply pipe 65, and is introduced into the enclosure.

The mud introduced into the enclosure 63 via the supply pipe 65 is evacuated by overflowing into the evacuation pipe 67 through the overflow passage 87. Furthermore, a portion of the evacuated mud temporarily resides in the siphon 93 of the evacuation pipe 67, which prevents gas from entering the upper portion 75 of the enclosure 63 through the lower end 97 of the evacuation pipe 67. The introduction of gas into the enclosure 63 therefore takes place solely through the introduction inlet.

The agitator 79 is driven in rotation by the motor 81, and agitates the mud in the lower portion 73 of the enclosure 63 in order to bring about the continuous extraction of the gases contained in the mud, and also the mixing of the extracted gases with the carrier gas introduced through the injection passage 99.

As specified previously, a stream of extracted gas is sampled continuously at the outlet 101 under the action of the suction caused by the pump 107. As specified above, the stream of extracted gases comprises $C_1$ to $C_n$ hydrocarbons to be analysed in the analyser 55, water vapour and polar interfering compounds such as alcohols, ethers or esters, these compounds resulting from the composition of the mud present in the injection means 43 or from the chemical reaction between the compounds constituting the mud when it circulates at the bottom of the well.

The gas stream is then conveyed through the water trap 103 in order to eliminate the water vapour present by condensation. The gas stream then flows through the flow rate controller 105. The controlled flow rate of gas stream circulating in the line 54 is then between 300 cm$^3$/min and 2000 cm$^3$/min.

Then approximately 10% of the gas stream is sampled through the branch connection 109, whereas approximately 90% of the gas stream is transported to the atmosphere through the pump.

The gas stream present in the branch connection 109 then circulates through the purification means 56. The gas stream is then introduced in the fitting 135 into the internal volume in order to circulate in contact with the interaction surface 141 present on the solid.

In contact with the interaction surface 141, the polar interfering compounds such as the alcohols, ethers or esters are retained by dipolar interaction, whereas the $C_1$ to $C_n$ hydrocarbons to be analysed circulate substantially freely.

The gas stream recovered continuously at the outlet fitting 137 of the purification means 56 therefore contains $C_1$ to $C_n$ hydrocarbons to be analysed, but is devoid of polar interfering compounds liable to have an elution time of between the elution time of the first hydrocarbon to be analysed and the elution time of the last hydrocarbon to be analysed in the separation column 121.

The gas stream is then introduced into the separation column 121, which permits the selective separation of the $C_1$ to $C_n$ hydrocarbons according to their elution time in the column 121.

Figure 4:
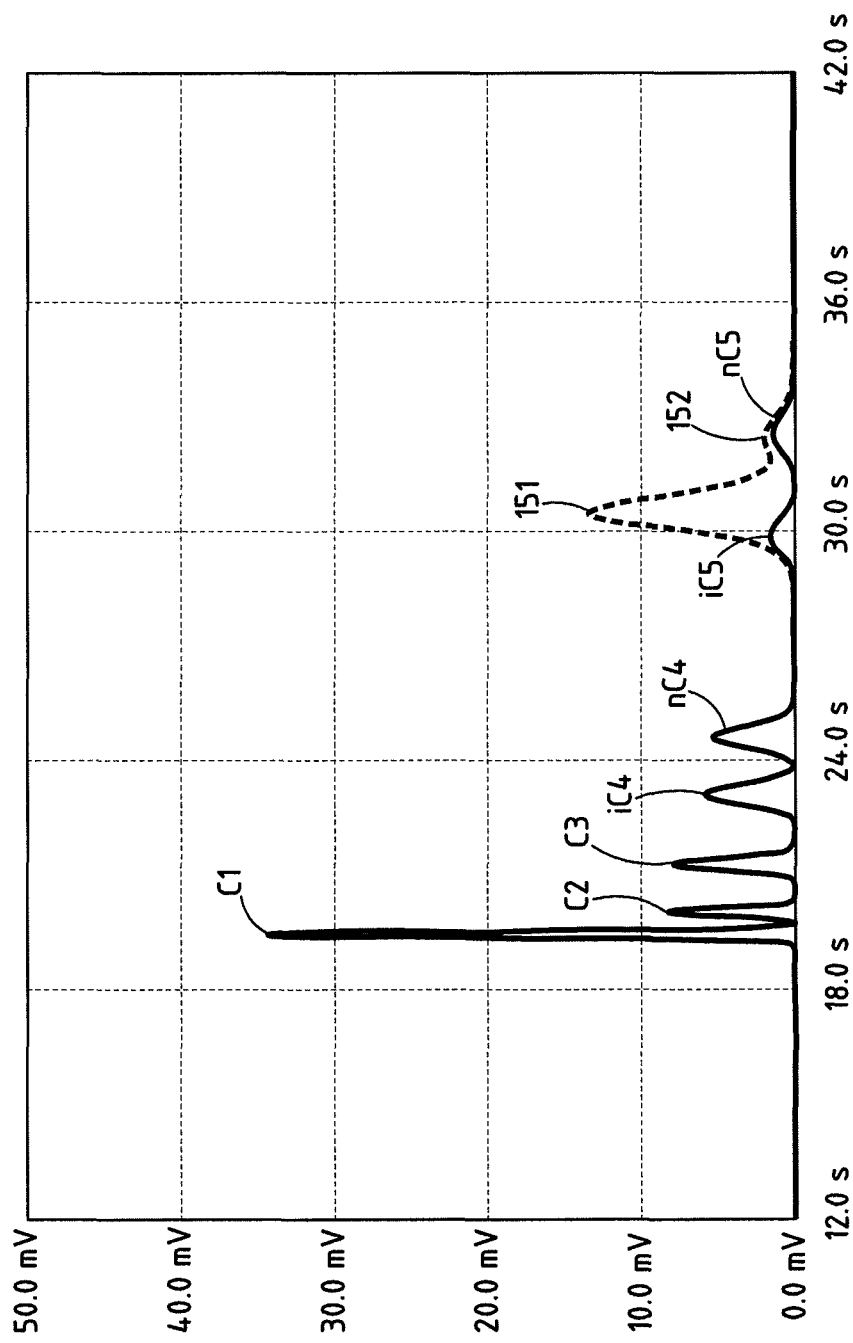
FIG. 4 is a view of a successive elution chromatogram of the $C_1$ to $C_5$ hydrocarbons measured when carrying out a method according to the invention, and, in comparison, when carrying out a method of the prior art.

The successive presence of these hydrocarbons is detected through the detector 123 as shown in FIG. 4, which illustrates the intensity recorded by the detector as a function of the elution time.

The first peak detected, on the left in FIG. 4, corresponds to the $C_1$ hydrocarbons, the second peak corresponds to the $C_2$ hydrocarbons, the third peak to the $C_3$ hydrocarbons, the fourth peak to the $iC_4$ hydrocarbons, the fifth peak to the $NC_4$ hydrocarbons, the sixth peak to the $iC_5$ hydrocarbons and the seventh peak to the $nC_5$ hydrocarbons.

By way of comparison, when the gas stream present upstream from the purification means 56 in the branch connection 109 is injected directly into the column 121, without passing through the purification means 56, the polar interfering compounds present in the gas stream before it has passed through have an elution time of between the elution time of the first hydrocarbon to be analysed, namely the $C_1$ hydrocarbons, and the elution time of the last hydrocarbon to be analysed, namely the $nC_5$ hydrocarbons. Consequently, two interfering peaks 151, 152, shown in broken lines in FIG. 4, are generated. These peaks mask the peaks corresponding to certain of the hydrocarbons to be analysed, such as, for example, those corresponding to the $iC_5$ and $nC_5$ hydrocarbons respectively.

Carrying out the method according to the invention therefore makes it possible to measure on-line, at the outlet of an extractor, the presence of $C_1$ to $C_n$ hydrocarbons in the gas stream extracted from the mud and to quantify at least the $C_1$ to $C_5$ hydrocarbons precisely, without measurement skew caused by the presence of interfering compounds of the alcohol, ether or ester type.

In one variant, a pre-selection column is interposed between the purification means 56 and the column 121. This preselection column is capable of selectively retaining the $C_m$ hydrocarbons, with m being greater than 10, which are not injected into the column 121.

Figure 5:
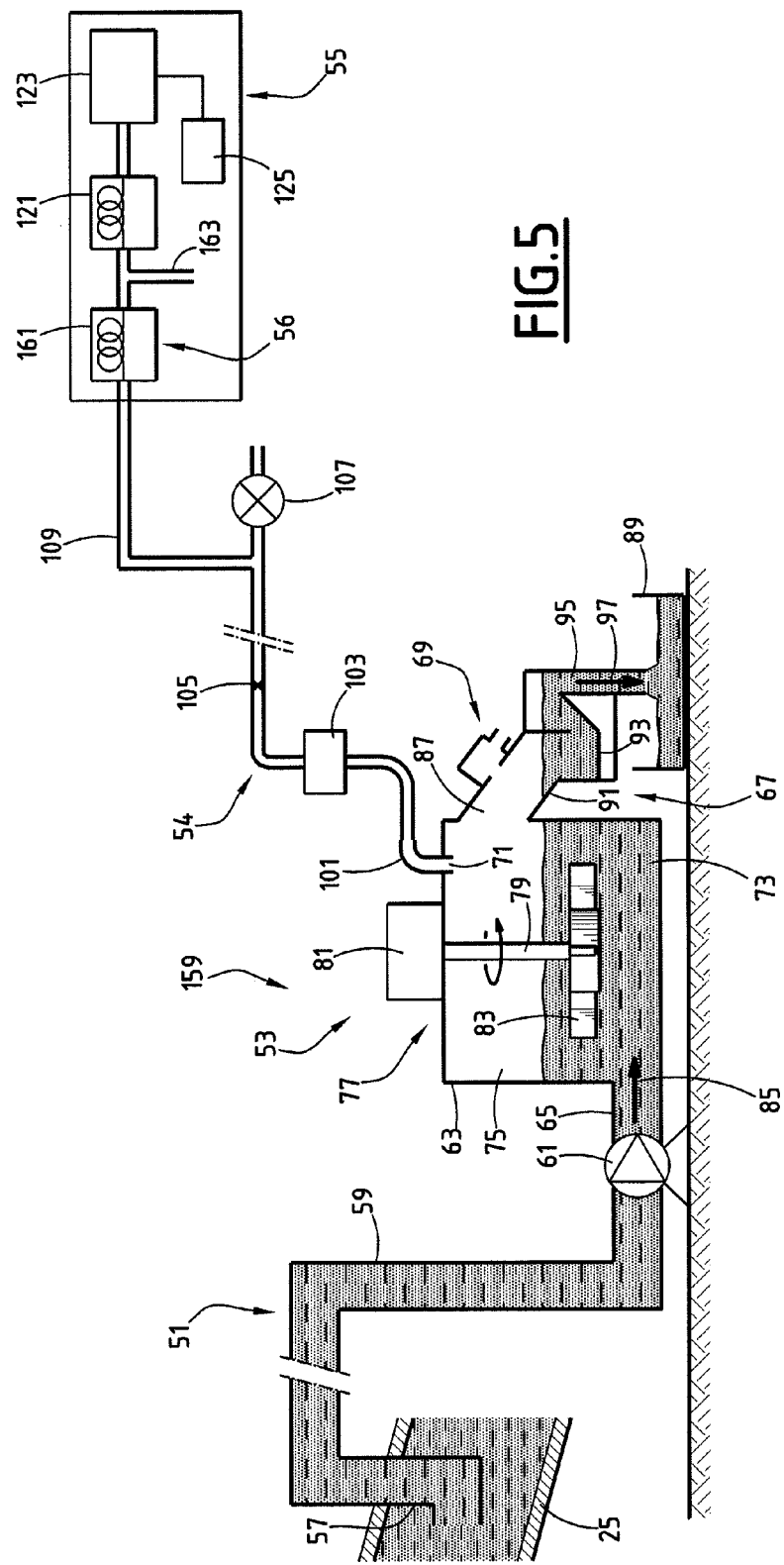
FIG. 5 is a view analogous to FIG. 2 of a second analysis unit according to the invention.

In the second analysis unit 159 according to the invention, shown in FIG. 5, the purification means 56 are formed by a pre-separation column 161 mounted at the inlet of the analyser 55 between the branch connection 109 and the separation column 121.

The pre-separation column is selected to offer not only selective retention of the $C_m$ hydrocarbons, with m being greater than 8, but also selective retention of the polar interfering compounds having an elution time in the separation column 121 of between the elution time of the first hydrocarbon to be analysed and the elution time of the last hydrocarbon to be analysed.

To this end, the pre-separation column 161 is advantageously filled with a polar gel which delimits the interaction surface 141. The column 161 filled with the polar gel has a "Chrompack" index of greater than 8, and advantageously greater than 20, as defined in "Manuel de Chromatographie en Phase Gazeuse", fourth edition, 1995, pages 366 and 373, published under the editorship of Jean Tranchant at Masson.

This Chrompack index is defined as the total of the five McReynolds constants for benzene, 1-butanol, 2-pentanone, nitropropane and pyridine. The McReynolds classification system is based on the measurement of the different retention indices of a series of 10 test substances (the first 5 of which are retained for calculating the Chrompack index) measured at the same temperature, on one hand on the phase to be tested in the column 161, and on the other hand on squalane. The total of the five constants gives the Chrompack index, which characterises the polarity, a low Chrompack index being characteristic of an apolar column and a high Chrompack index being characteristic of a polar column.

Such a column operates by selective solubilisation of the polar interfering compounds in the gel constituting the column relative to the hydrocarbons. Such a column comprises for example a stationary phase produced on the basis of a polyethylene glycol gel.

Thus, when a gas stream containing hydrocarbons to be analysed and polar interfering compounds is introduced into the pre-separation column 161, then circulates in the column 161 at a flow rate of between 5 cm³ per minute and 200 cm³ per minute, more than 90 mole % of the hydrocarbons to be analysed exit from the column 161, whereas less than 10% of the polar interfering compounds exit from the column 161 after a time equal to twice the dwell time in the column 161.

The pre-separation column 161 is connected at the outlet to the separation column 121 and to a purging pipe 163 with the aid of a three-way valve which makes it possible to purge selectively, after a given time, a portion of the compounds emerging from the pre-separation column 161.

The analysis method carried out in the second unit 159 according to the invention differs from the method carried out in the first unit 19 in that the gas stream extracted from the mud containing the hydrocarbons to be analysed and the polar interfering compounds passes into the pre-separation column 161 before entering the column 121.

As it passes through, substantially all of the $C_1$ to $C_n$ hydrocarbons, with n being less than or equal to 10, advantageously n being less than or equal to 8, are free to pass, whereas substantially all of the $C_m^+$ hydrocarbons, with m being greater than 10, and the polar interfering compounds liable to have a retention time in the column 121 comparable to that of the $C_1$ to $C_n$ hydrocarbons are retained in the pre-separation column 161.

After a given time, when all the $C_1$ to $C_n$ hydrocarbons have emerged from the pre-separation column 161 and have been introduced into the separation column 121, the outlet of the pre-separation column 161 is connected to the purging pipe 163 by means of the three-way valve in order to purge the column 161 and evacuate the compounds which would not be definitively retained by this column.

In a variant, the pre-separation column 161 comprises a solid coating which interacts selectively with the polar compounds to be eliminated by hydrogen bonds or by dipolar interactions.

In one variant, the pre-separation column 161 is charged with an interaction surface 141 in solid form, formed from unmodified silica, silica modified with electron donor groups, as defined above, silica doped with magnesium, alumina or a styrene/divinylbenzene polymer.

In one variant, the extractor 53 is formed by a hollow stem immersed in the mud and having a porous wall forming an extraction membrane for the gases contained in the mud. The hollow stem is connected to an analyser 55 by a pipe of short length.

The purification means 56 described previously are then placed between the extraction membrane and the separation column 121 of the analyser 55.

The interaction within the column 161 is advantageously a dipole-dipole interaction or a London dispersion force interaction.

Advantageously, the pre-separation column 161 has a stationary phase containing a salt, such as a salt comprising at least one alkaline earth element.

The invention claimed is:

1. A method for analysing a plurality of hydrocarbons contained in a drilling fluid, of the type comprising the following steps:
   - extraction of the gases contained in the fluid in an extractor in order to obtain continuously, at an outlet of the extractor, a gas stream of extracted gases containing hydrocarbons to be analysed and at least one interfering compound other than water and more polar than the hydrocarbons to be analysed;
   - transport of the gas stream through a transport line connected to the outlet of the extractor;
   - passing of the gas stream into a separation column connected to the transport line, in order to separate the hydrocarbons to be analysed according to their elution time in the separation column;
   - successive detection and/or quantification of each hydrocarbon to be analysed in a detector placed at the outlet of the separation column;
   - the or each interfering compound having an elution time in the separation column of between the elution time in the separation column of the first hydrocarbon to be analysed and the elution time in the separation column of the last hydrocarbon to be analysed;
   - wherein the method comprises the step of passing the gas stream over a surface of chemical and/or physical interaction with the interfering compound, the interaction surface being placed in contact with the gases between the outlet of the extractor and an inlet of the separation column, to retain selectively the or each interfering compound without retaining the hydrocarbons to be analysed, in order to prevent the elution of the or each interfering compound in the separation column between the elution time of the first hydrocarbon to be analysed and the elution time of the last hydrocarbon to be analysed.

2. The method according to claim 1, wherein the interaction surface is suitable for interacting with the or each interfering compound via a hydrogen-bond, dipolar-attraction or ion-exchange mechanism, in order to retain selectively the or each interfering compound without retaining each hydrocarbon to be analysed.

3. The method according to claim 1, wherein when the gas stream passes over the interaction surface, more than 90 mole % of each polar interfering compound is retained on the interaction surface, less than 10 mole % of the hydrocarbons to be analysed being retained on the interaction surface.

4. The method according to claim 1, wherein the interaction surface comprises unmodified silica, silica modified with electron donor groups, silica doped with magnesium, alumina, or a styrene/divinylbenzene polymer.

5. The method according to claim 1, wherein the interaction surface is placed in a removable cartridge mounted on the transport line between the outlet of the extractor and the separation column.

6. The method according to claim 1, wherein the hydrocarbons to be analysed comprise $C_1$ to $C_n$ hydrocarbons, n being less than or equal to 10, advantageously n being less than or equal to 8.

7. The method according to claim 1, wherein the or each polar interfering compound comprises at least an oxygen atom, a nitrogen atom or a sulphur atom.

8. The method according to claim 1, wherein the interaction surface is arranged in a pre-separation column mounted upstream from the separation column.

9. The method according to claim 8, wherein the interaction surface comprises polyethylene glycol.

10. The method according to claim 8, wherein the pre-separation column has a Chrompack index of greater than 8, advantageously greater than 20.

11. A unit for the analysis of a plurality of hydrocarbons contained in a drilling fluid, of the type comprising:
   - an extractor for the gases contained in the fluid, the extractor having a gas extraction outlet in order to obtain, continuously at the outlet, a gas stream of extracted gases containing hydrocarbons to be analysed and at least one interfering compound other than water and more polar than the hydrocarbons to be analysed;
   - a transport line for the gas stream, connected to the outlet of the extractor;

an analyser comprising:
- a separation column connected to the transport line for separating the hydrocarbons to be analysed according to their elution time in the separation column;
- a detector placed at the outlet of the separation column for detecting and/or quantifying in succession each hydrocarbon to be analysed;

the interfering compound having an elution time in the separation column of between the elution time in the separation column of the first hydrocarbon to be analysed and the elution time in the separation column of the last hydrocarbon to be analysed, wherein that the analysis unit comprises a surface of chemical and/or physical interaction with the interfering compound, the interaction surface being placed in contact with the gases between the outlet of the extractor and an inlet of the separation column, in order to retain selectively the or each interfering compound without retaining the hydrocarbons to be analysed, in order to prevent the elution of the or of each interfering compound in the separation column between the elution time of the first hydrocarbon to be analysed and the elution time of the last hydrocarbon to be analysed.

12. The unit according to claim 11, wherein it comprises a removable cartridge containing the interaction surface, the removable cartridge being mounted in series on the transport line upstream from the separation column.

13. The unit according to claim 11, wherein it comprises a pre-separation column containing the interaction surface, the pre-separation column being mounted in series on the transport line or downstream from the transport line, upstream from the separation column.

\* \* \* \* \*